United States Patent
Kollgaard et al.

(10) Patent No.: US 10,222,353 B2
(45) Date of Patent: Mar. 5, 2019

(54) METHOD AND ASSEMBLY FOR INSPECTING A PARTIALLY CURED REPAIR PATCH PRIOR TO INSTALLATION

(71) Applicant: The Boeing Company, Chicago, IL (US)

(72) Inventors: Jeffrey Reyner Kollgaard, Seattle, WA (US); John F. Spalding, Tukwilla, WA (US)

(73) Assignee: THE BOEING COMPANY, Chicago, IL (US)

( * ) Notice: Subject to any disclaimer, the term of this patent is extended or adjusted under 35 U.S.C. 154(b) by 316 days.

(21) Appl. No.: 14/661,417

(22) Filed: Mar. 18, 2015

(65) Prior Publication Data

US 2016/0274063 A1 Sep. 22, 2016

(51) Int. Cl.
*G01H 9/00* (2006.01)
*G01H 1/00* (2006.01)
(Continued)

(52) U.S. Cl.
CPC ............ *G01N 29/09* (2013.01); *B29C 70/342* (2013.01); *B29C 73/10* (2013.01); *B29C 73/12* (2013.01);
(Continued)

(58) Field of Classification Search
CPC ............. G01N 29/09; G01N 2291/018; G01N 2291/023; G01N 2291/0289; G01N 25/72;
(Continued)

(56) References Cited

U.S. PATENT DOCUMENTS 3,996,085 A * 12/1976 Barnes .................... B29C 73/06
152/367
4,357,193 A 11/1982 McGann et al.
(Continued)

FOREIGN PATENT DOCUMENTS

CA 2127039 A1 3/1996
DE 10 2006 001494 B3 8/2007
(Continued)

OTHER PUBLICATIONS

Ultrasonic process for curing adhesives, Senapati et al., Mar. 1993.*
(Continued)

*Primary Examiner* — J M Saint Surin
(74) *Attorney, Agent, or Firm* — Alston & Bird LLP

(57) ABSTRACT

A method and assembly are provided in order to inspect a partially cured repair patch prior to installation. For example, an assembly for inspecting a repair patch is provided that includes a partially cured repair patch comprised of a composite material. The assembly also includes an acoustic facilitation layer disposed proximate of the surface of the repair patch through which ultrasonic signals will be introduced. The assembly further includes a vacuum bag surrounding the repair patch and the acoustic facilitation layer. The acoustic facilitation layer has an acoustic impedance that is closer to the respective acoustic impedances of the repair patch and the vacuum bag than the acoustic impedance of air is to the respective acoustic impedances of the repair patch and the vacuum bag.

20 Claims, 4 Drawing Sheets

(51) Int. Cl.
*G01N 29/28* (2006.01)
*B29C 70/34* (2006.01)
*B29C 73/10* (2006.01)
*B29C 73/12* (2006.01)
*G01N 29/09* (2006.01)
*G10K 11/02* (2006.01)

(52) U.S. Cl.
CPC ............... *G01H 1/00* (2013.01); *G01H 9/008* (2013.01); *G01N 29/28* (2013.01); *G01N 2291/018* (2013.01); *G01N 2291/023* (2013.01); *G01N 2291/0231* (2013.01); *G01N 2291/0289* (2013.01); *G01N 2291/044* (2013.01); *G01N 2291/048* (2013.01); *G10K 11/02* (2013.01)

(58) Field of Classification Search
CPC .... G01N 29/043; G01N 29/22; B29C 70/342; B29C 73/12; B29C 73/10; B29C 70/44
USPC .......................................................... 73/571
See application file for complete search history.

(56) References Cited

U.S. PATENT DOCUMENTS

| | | | |
|---|---|---|---|
| 5,009,104 A | 4/1991 | Johnson | |
| 5,442,156 A | 8/1995 | Westerman et al. | |
| 5,709,469 A | 1/1998 | White et al. | |
| 5,958,166 A | 9/1999 | Walters et al. | |
| 6,149,749 A | 11/2000 | McBroom | |
| 6,206,067 B1 | 3/2001 | Kociemba et al. | |
| 6,234,025 B1* | 5/2001 | Gieske | G01N 29/221 73/629 |
| 6,270,603 B1 | 8/2001 | Westerman et al. | |
| 6,435,242 B1 | 8/2002 | Reis et al. | |
| 6,468,372 B2 | 10/2002 | Kociemba et al. | |
| 6,761,783 B2 | 7/2004 | Keller et al. | |
| 7,137,799 B2 | 11/2006 | Banasky | |
| 8,356,649 B2* | 1/2013 | Cacace | B29C 73/10 156/285 |
| 8,371,009 B2* | 2/2013 | Xie | B29C 73/04 29/402.09 |
| 8,540,909 B2* | 9/2013 | Dan-Jumbo | B29C 73/10 156/94 |
| 8,707,766 B2* | 4/2014 | Harris | G01N 31/225 264/571 |
| 8,790,485 B2* | 7/2014 | Whitworth | B29C 65/18 156/285 |
| 8,936,695 B2* | 1/2015 | Rotter | B29C 70/382 100/269.02 |
| 8,986,479 B2* | 3/2015 | Evens | B29C 73/10 156/285 |
| 9,492,975 B2* | 11/2016 | Dan-Jumbo | B29C 73/10 |
| 2002/0189359 A1 | 12/2002 | Batzinger et al. | |
| 2003/0188821 A1 | 10/2003 | Keller et al. | |
| 2004/0035208 A1* | 2/2004 | Diaz | G01N 29/024 73/597 |
| 2006/0191624 A1 | 8/2006 | Whitworth et al. | |
| 2007/0017297 A1 | 1/2007 | Georgeson et al. | |
| 2007/0095457 A1 | 5/2007 | Keller et al. | |
| 2007/0100582 A1* | 5/2007 | Griess | G01M 5/0033 702/183 |
| 2008/0099053 A1* | 5/2008 | Loveless | A47L 7/0004 134/21 |
| 2008/0308210 A1 | 12/2008 | Keller et al. | |
| 2009/0166346 A1 | 7/2009 | Ketelhut et al. | |
| 2010/0024958 A1 | 2/2010 | Sawicki et al. | |
| 2010/0243152 A1 | 9/2010 | Helfrich et al. | |
| 2010/0244327 A1* | 9/2010 | Byrd | B01J 3/006 264/443 |

FOREIGN PATENT DOCUMENTS

| | | | |
|---|---|---|---|
| DE | 102007026099 | * | 11/2008 |
| DE | 10 2007 026099 A1 | | 12/2008 |
| DE | 10 2008 051380 A1 | | 4/2010 |
| DE | 2008051380 | * | 4/2010 |
| WO | WO2012050712 | * | 4/2012 |

OTHER PUBLICATIONS

Extended European Search Report for corresponding European Application No. 16159918.8 dated Aug. 19, 2016, 9 pages.
International Search Report and Written Opinion for Application No. PCT/US2011/051496 dated Mar. 30, 2012.
*Acoustic Properties of Rubbers*, Onda Corporation (Apr. 11, 2003), 3 pages.
Ginzel, E. a. et al., *Ultrasonic Properties of a New Low Attenuation Dry Couplant Elastomer*, Ginzel Brothers & Associates Ltd. (Apr. 1994) 10 pages.
*B-stage Epoxy*, Tech 20 Tip, Epoxy Technology, Inc. (Brochure) (2012), 2 pages.
Ginzel, E. A. et al., *A New elastomeric Wedge or Delayline Material* (dated Feb. 2009) 1 page abstract, 5 pages of article.

* cited by examiner

METHOD AND ASSEMBLY FOR INSPECTING A PARTIALLY CURED REPAIR PATCH PRIOR TO INSTALLATION

TECHNOLOGICAL FIELD

An example embodiment is directed to a method and assembly for inspecting a repair patch and, more particularly, to a method and assembly for inspecting a partially cured repair patch prior to installation.

BACKGROUND

Repair patches are utilized to repair of a variety of structures, such as vehicles including aircraft, water vehicles or the like, as well as buildings and other structures. In this regard, a repair patch may be comprised of a composite material, such as carbon fibers embedded in an epoxy matrix, with the composite repair patch being adhered to the structure in order to affect the repair.

Repair patches comprised of a composite material may be partially cured prior to the installation of the repair patches upon the structure. In this regard, a repair patch may be debulked and consolidated, such as in accordance with a double vacuum debulk (DVD) process, prior to its installation. As a result of the partial curing of the repair patch, however, porosity or delaminations may be disadvantageously introduced into the repair patch, which may adversely impact the performance and longevity of the repair patch following its installation. For example, porosity may be introduced as a result of the inclusion of an expired material, or as a result of a vacuum leak or an impropriety with respect to the cure temperature or another cure parameter.

Once the repair patch has been partial cured, the repair patch may be installed in order to repair the structure. In this regard, the repair patch may be adhered to the structure and then subjected to a final curing process once in place upon the structure. Following the installation of the repair patch, the repair patch may be inspected to determine, among other parameters, the porosity of the repair patch and the bond line defined by the adhesive between the repair patch and the structure. In an instance in which the repair patch and/or the bond line fails to satisfy the predefined requirements associated with the successful installation of a repair patch, such as in an instance in which the repair patch and/or the bond line has excessive porosity, the repair patch may be removed, the surface of the structure reworked and another repair patch installed. The process of removing an unsuccessful repair patch and reworking the surface of the structure prior to installing another repair patch may be a time consuming and expensive process that delays the eventual reentry of the structure into service.

By inspecting the repair patch following its installation, it is also difficult to discriminate between issues, such as excessive porosity, that are attributable to the repair patch or that are attributable to the bond line between the repair patch and the structure, or are attributable to geometric variations and surface coatings of the structure lying behind the repair patch. Moreover, with respect to the porosity of the repair patch, the inspection of the repair patch following the installation of the repair patch may prevents technician from determining whether the porosity was introduced during the partial curing of the repair patch prior to installation or during the final curing of the repair patch. Consequently, it may be difficult to determine with accuracy any systemic changes to the repair process that should be introduced.

BRIEF SUMMARY

A method and assembly are provided in accordance with an example embodiment in order to inspect a partially cured repair patch prior to installation. By inspecting the repair patch prior to installation, but following the partial curing of the repair patch, the method and assembly may ensure that only repair patches that are installed are repair patches that satisfy predetermined requirements, such as by having a sufficiently low level of porosity, being without delaminations and including no or an acceptable level of foreign object inclusions, at the inception of the installation process. Thus, the method and assembly may avoid the installation of repair patches that already fail to satisfy the predetermined requirements, such as by having unacceptably high porosity, having delaminations or including more than an acceptable level of foreign object inclusions, prior to the commencement of the installation and, as such, may reduce the percentage of installed repair patches that must be removed and replaced. As a result of the inspection of the repair patch prior to installation, the subsequent inspection of the repair patch after final bonding is simplified, since the inspection following final bonding may, in some embodiments, be focused upon flaws at the bond line without having to perform the arduous porosity inspection upon the repair patch.

In an example embodiment, an assembly for inspecting a repair patch is provided. The assembly includes a partially cured repair patch comprised of a composite material. The assembly also includes an acoustic facilitation layer disposed proximate of the surface of the repair patch through which ultrasonic signals will be introduced. The assembly further includes a vacuum bag surrounding the repair patch and the acoustic facilitation layer. The acoustic facilitation layer has an acoustic impedance that is closer to the respective acoustic impedances of the repair patch and the vacuum bag than the acoustic impedance of air is to the respective acoustic impedances of the repair patch and the vacuum bag. For example, the acoustic facilitation layer may be comprised of a silicon-based synthetic rubber, a silicon rubber, a butyl-rubber, neoprene, urethane rubber or a combination thereof.

The assembly of an example embodiment also includes an ultrasonic transducer configured to introduce ultrasonic signals through the vacuum bag and the acoustic facilitation layer and then into the repair patch. The ultrasonic transducer of this example embodiment is also configured to receive echo signals returning from the repair patch to facilitate single-sided inspection of the repair patch. The vacuum bag of an example embodiment is configured to apply pressure to the acoustic facilitation layer and the repair patch during the single-sided inspection of the repair patch. The pressure enhances the intimate contact between the vacuum bag and the acoustic facilitation layer and improves ultrasonic transmission.

The assembly of an example embodiment also includes a second acoustic facilitation layer disposed proximate a second surface of the repair patch, opposite the surface of the repair patch through which ultrasonic signals will be introduced. The assembly of this example embodiment also includes an ultrasonic transducer configured to introduce ultrasonic signals that propagate through the vacuum bag, both acoustic facilitation layers and the repair patch so as to facilitate through transmission inspection repair patch.

In another example embodiment, an assembly for inspecting a repair patch is provided. The assembly includes a partially cured repair patch comprised of a composite material. The assembly also includes a vacuum bag surrounding the repair patch and making direct contact with the repair patch so as to define an interface directly between the vacuum bag and the repair patch. The vacuum bag is comprised of an acoustic facilitation material which has an acoustic impedance that is closer to the acoustic impedance of the repair patch than the acoustic impedance of air is to the acoustic impedance of the repair patch. For example, the vacuum bag may be comprised of a silicon-based synthetic rubber, a silicon rubber, a butyl-rubber, a neoprene, urethane rubber or a combination thereof.

The assembly of an example embodiment also includes an ultrasonic transducer configured to introduce ultrasonic signals through the vacuum bag and then into the repair patch. The ultrasonic transducer of this example embodiment is further configured to receive echo signals returning from the repair patch to facilitate single-sided inspection of the repair patch. The vacuum bag of this example embodiment is configured to apply pressure to the repair patch during the single-sided inspection of the repair patch. In an alternative embodiment, the assembly further includes an ultrasonic transducer configured to introduce ultrasonic signals that propagate through the vacuum bag and the repair patch so as to facilitate through transmission inspection of the repair patch.

In a further example embodiment, a method of inspecting a partially cured repair patch is provided. The method includes placing the repair patch within a vacuum bag such that an acoustic facilitation material makes direct contact with the repair patch so as to define an interface directly between the acoustic facilitation material and the repair patch. The acoustic facilitation material has an acoustic impedance that is closer to the acoustic impedance of the repair patch than the acoustic impedance of air is to the acoustic impedance of the repair patch. The method also includes transmitting ultrasonic signals such that the ultrasonic signals are introduced into the repair patch after propagating through the acoustic facilitation material. The method further includes receiving the ultrasonic signals following interaction with the repair patch and propagation through the acoustic facilitation material and determining integrity of the repair patch based upon the ultrasonic signals that are received.

The method of an example embodiment also includes disposing an acoustic facilitation layer comprised of the acoustic facilitation material proximate the surface of the repair patch through which the ultrasonic signals will be introduced. In this embodiment, the repair patch is placed within the vacuum bag by placing the repair patch and the acoustic facilitation layer within the vacuum bag. The method of this example embodiment is configured to perform the transmission and reception of ultrasonic signals from a single side of the repair patch.

The method of an example embodiment also includes disposing an acoustic facilitation layer comprised of the acoustic facilitation material proximate the surface of the repair patch through which the ultrasonic signals will be introduced. The method of this example embodiment also includes disposing a second acoustic facilitation layer proximate a second surface of the repair patch, opposite the surface of the repair patch through which the ultrasonic signals will be introduced. In this example embodiment, the repair patch is placed within the vacuum bag by placing the repair patch with the acoustic facilitation layers disposed proximate opposite surfaces thereof within the vacuum bag. The method of this example embodiment also receives the ultrasonic signals by receiving ultrasonic signals that exit from a surface of the repair patch, opposite the surface through which the ultrasonic signals are introduced into the repair patch.

The method of an example embodiment also includes determining whether the integrity of the repair patch satisfies the predefined criteria. In an instance in which the integrity of the repair patch satisfies the predefined criteria, the method further includes applying the repair patch to a structure and further curing the repair patch. However, in an instance in which the integrity of the repair patch fails to satisfy the predefined criteria, the method further includes discarding or reworking the repair patch.

In an example embodiment, the vacuum bag is comprised of the acoustic facilitation material. The acoustic facilitation material of an example embodiment is comprised of a silicon-based synthetic rubber, a silicon rubber, a butyl-rubber, a neoprene, urethane rubber or a combination thereof. The repair patch of an example embodiment has been debulked and consolidated prior to being placed within the vacuum bag.

BRIEF DESCRIPTION OF THE DRAWINGS

Figure 1:
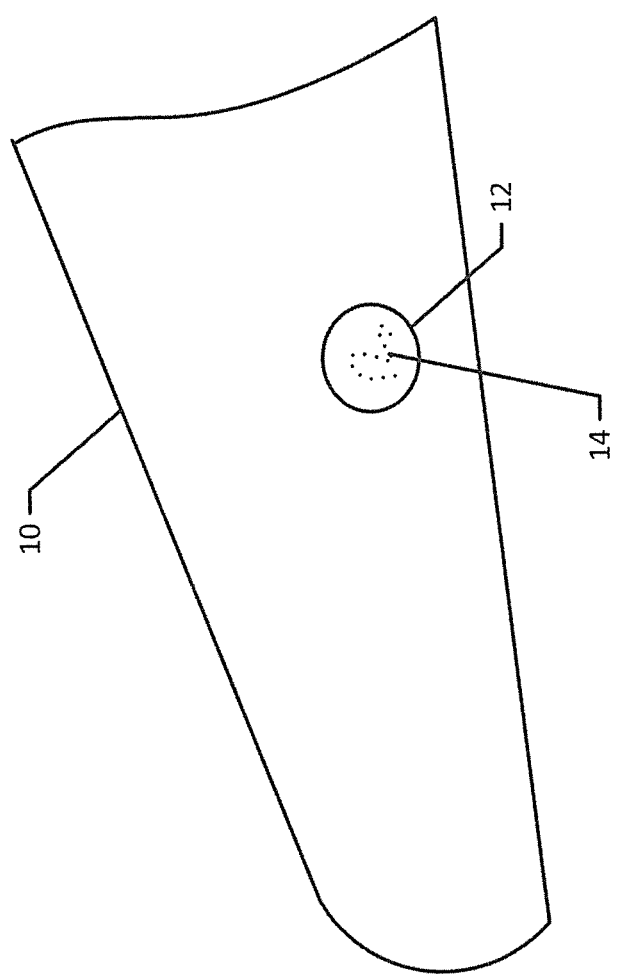
Figure 2:
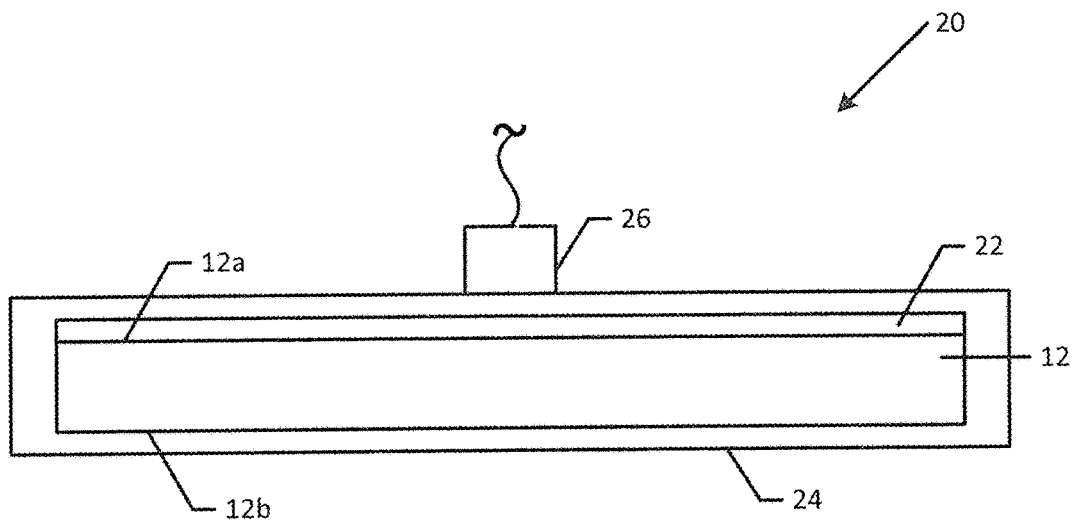
Figure 3:
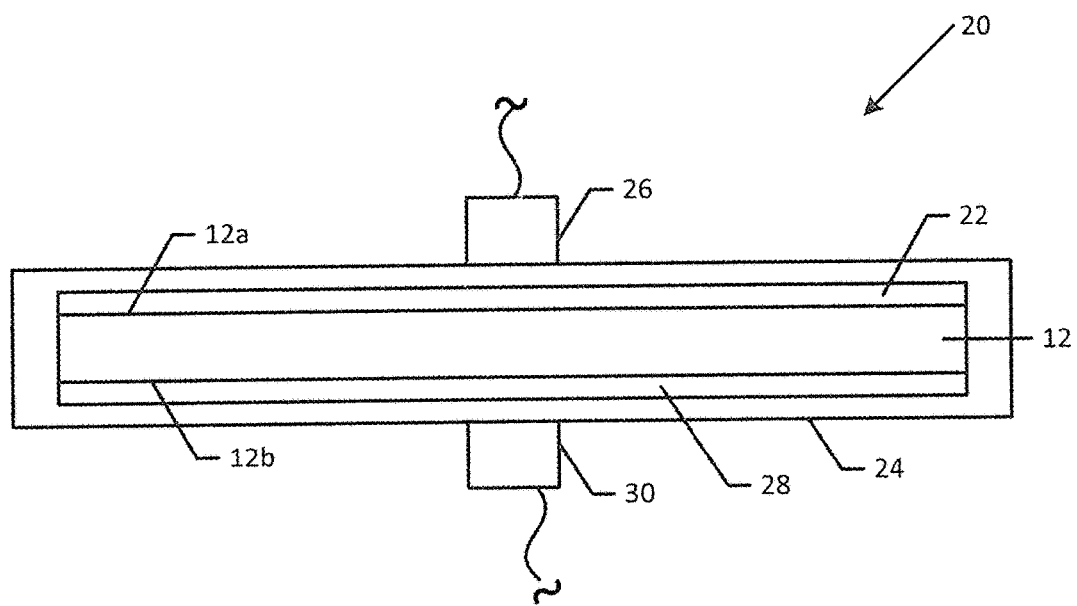
Figure 4:
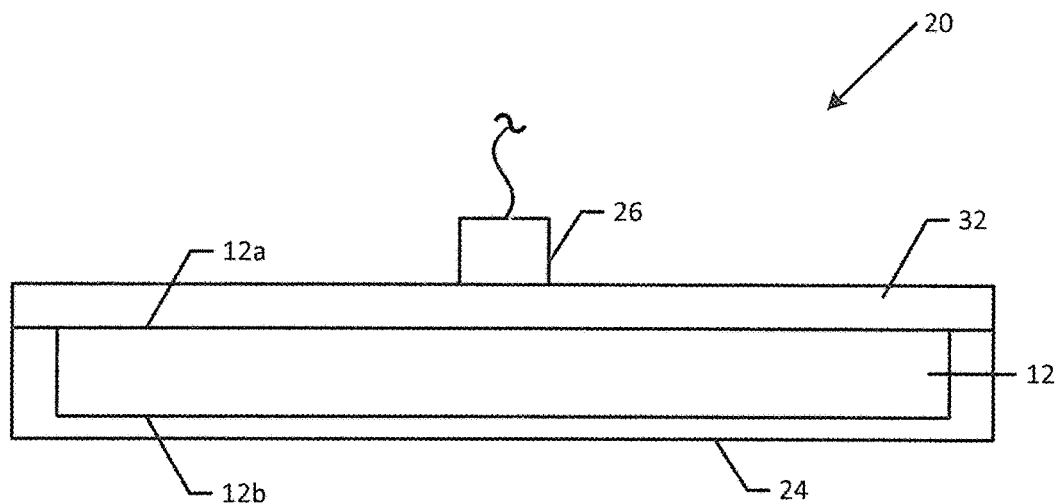
Figure 5:
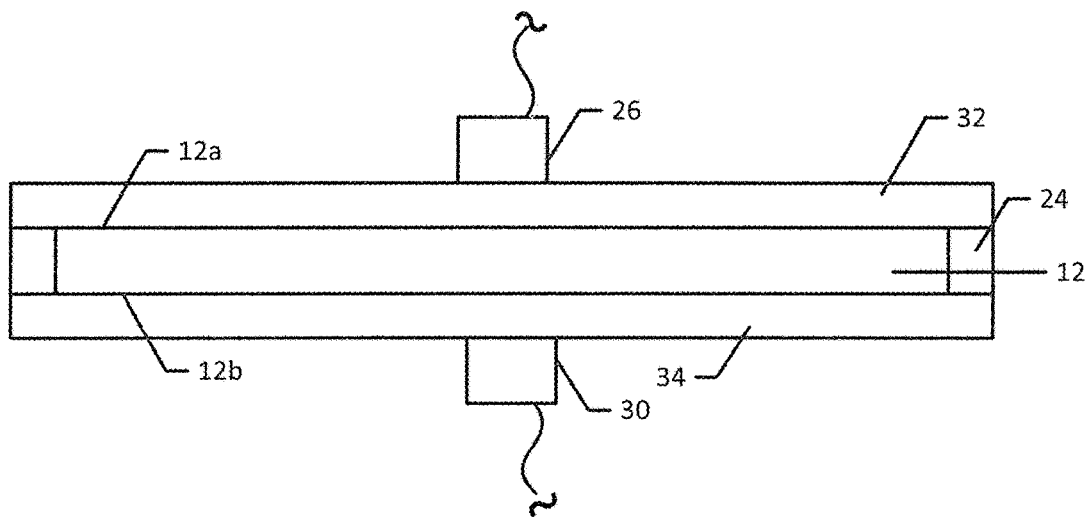
Figure 6:
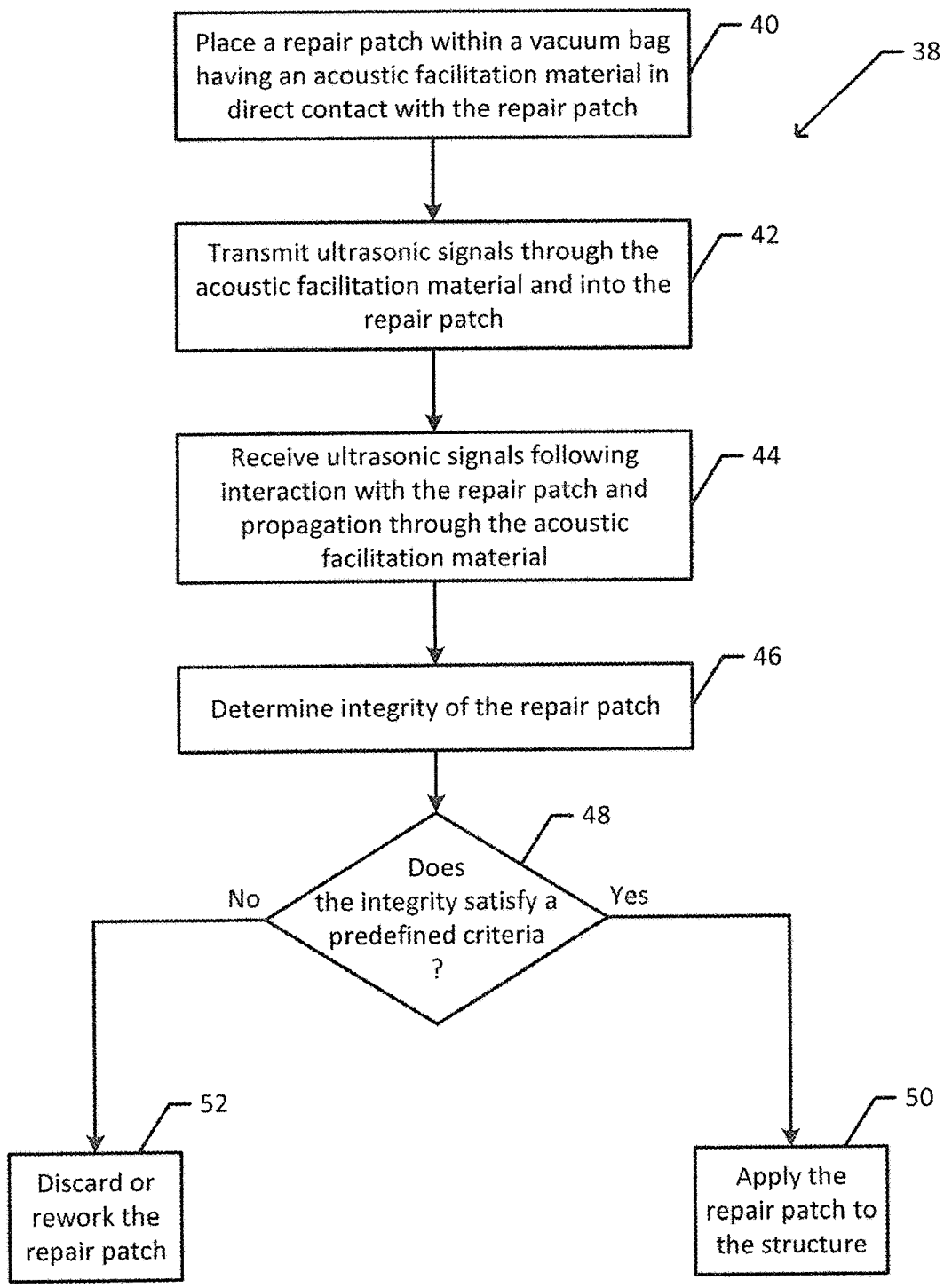

Having thus described certain example embodiments of the present disclosure in general terms, reference will hereinafter be made to the accompanying drawings, which are not necessarily drawn to scale, and wherein:

FIG. 1 is a perspective view of a portion of a wing of an aircraft having a repair patch installed thereupon;

FIG. 2 is a cross-sectional view of a repair patch in accordance with an example embodiment of the present disclosure;

FIG. 3 is a cross-sectional view of a repair patch in accordance with another example embodiment of the present disclosure;

FIG. 4 is a cross-sectional view of a repair patch in accordance with a further example embodiment of the present disclosure;

FIG. 5 is a cross-sectional view of a repair patch in accordance with yet another example embodiment of the present disclosure; and FIG. 6 is a flowchart illustrating operations performed in accordance with an example embodiment of the present disclosure.

DETAILED DESCRIPTION

The present disclosure now will be described more fully hereinafter with reference to the accompanying drawings, in which some, but not all aspects are shown. Indeed, the disclosure may be embodied in many different forms and should not be construed as limited to the aspects set forth herein. Rather, these aspects are provided so that this disclosure will satisfy applicable legal requirements. Like numbers refer to like elements throughout.

An assembly for inspecting a repair patch and the associated method are provided in accordance with an example embodiment of the present disclosure. In this regard, the repair patch may be utilized in order to repair a variety of structures, such as vehicles, including aircraft, watercraft or the like, etc. By way of example, FIG. 1 depicts a portion of a wing 10 of an aircraft to which a repair patch 12 has been affixed, such as with an adhesive, in order to repair a defect 14 shown in dashed lines in the wing. By repairing structures, such as the aircraft wing 10 of FIG. 1, with repair patches 12, these structures may be repaired in the field so as to reduce the time, if any, that the structure is out of service.

The repair patch 12 is generally formed of a composite material, such as a thermoset composite material, embodied by one or more plies of the composite material. While the repair patch 12 may be formed of plies of various types of composite materials, the repair patch of an example embodiment is comprised of plies formed of carbon fibers embedded in an epoxy matrix.

In accordance with an example embodiment, the repair patch 12 is inspected prior to installation on the structure. If the repair patch 12 is acceptable, the repair patch is adhered to the structure and the repair patch, and the resulting bond line to which the repair patch is affixed to the structure, are generally again inspected following affixation of the repair patch to ensure that the repair patch and the bond line are acceptable, such as by having sufficient structural integrity. Parameters that are considered in regards to the structural integrity of the repair patch 12 include the inspection of the repair patch and the bond line to determine the porosity of the repair patch and the bond line, to determine the presence of delaminations within the repair patch and/or to determine the presence of one or more foreign object inclusions, such as ply backing paper, within the repair patch. Repair patches 12 and bond lines having a porosity that exceeds a predetermined threshold, delaminations that exceed a predetermined limit, or a number of foreign object inclusions that exceed a predetermined value, may be considered unacceptable and, as such, may be removed and replaced with another repair patch having improved integrity.

By inspecting the repair patch 12 prior to its installation, the assembly and method for inspecting a repair patch can ensure that the repair patch satisfies the predefined requirements indicative of a suitable repair patch, such as by having an integrity that satisfies a predefined threshold, e.g., porosity that is less than the predefined threshold and an acceptably small number of delaminations and foreign object inclusions, prior to expending the time and resources required to install the repair patch. Thus, repair patches 12 that do not satisfy the predefined requirements can be discarded or reworked prior to installation so as to avoid the installation and likely subsequent removal of a repair patch that was unsatisfactory even prior to the installation.

Prior to the inspection, the repair patch 12 is generally appropriately sized, such as by being cut to the desired size and then partially cured. For example, the repair patch 12 may be debulked and consolidated in order to eliminate at least some of the air and volatiles between plies or preimpregnated laminates under moderate heat and vacuum, such as by a DVD process, to produce a B-stage repair patch. In this regard, a DVD process may involve laying up the repair patch 12, vacuum bagging the repair patch, placing the bagged patch in a rigid box, evacuating the box, applying an elevated temperature (lower than the cure temperature), allowing the patch to outgas from the vacuum bag through a vent tube to the environment, restoring atmospheric pressure to the box, and compressing the repair patch to consolidate the outgassed material. During the partial curing of the repair patch, the porosity of the repair patch 12 may increase. Following the partial curing of the repair patch 12, the repair patch may be inspected in accordance with an example embodiment of the present disclosure. In this regard, the partially cured repair patch 12 may be inspected by placing the repair patch within a vacuum bag with an acoustic facilitation material disposed proximate a surface of the repair patch, as described in more detail below.

Referring now to FIG. 2, an assembly 20 for inspecting a repair patch 12 is illustrated in accordance with an example embodiment. The assembly 20 includes a partially cured repair patch 12 formed of a composite material. The assembly 20 of this example embodiment also includes an acoustic facilitation layer 22 proximate the surface of the repair patch 12 through which ultrasonic signals will be introduced, as described below. In this regard, the repair patch 12 of an example embodiment includes opposed first and second surfaces 12a, 12b with the ultrasonic signals being introduced via the first surface as described below. As such, the acoustic facilitation layer 22 may be disposed proximate the first surface 12a of the repair patch 12 and, in an example embodiment, may be disposed in contact with the first surface 12a of the repair patch 12 so as to extend across the entire first surface.

The acoustic facilitation layer 22 is comprised of a material that facilitates the propagation of the ultrasonic signals into the repair patch 12 and reduces reflections from the surface 12a of the repair patch. Additionally, the acoustic facilitation layer 22 is comprised of a material that forms intimate, direct contact with the first surface 12a of the repair patch 12, thereby defining a single interface between the acoustic facilitation layer and the repair patch. This single interface is in contrast to the additional interface that would be created if the acoustic facilitation layer 22 were not in intimate contact with the first surface 12a of the repair patch 12 and if, instead, a layer of air existed therebetween. As ultrasonic signals reflect from the interfaces between materials having different acoustic impedances, the definition of a single interface between the acoustic facilitation layer 22 and the repair patch 12 increases the percentage of the ultrasonic signals that are transmitted into the repair patch relative to an instance in which a layer of air is adjacent the first surface 12a of the repair patch. Indeed, the direct contact of the acoustic facilitation layer 22 with the first surface 12a of the repair patch 12 eliminates the additional interface otherwise created by a layer of air which would cause an increased percentage of the acoustic signals to be reflected.

As shown in FIG. 2, the assembly 20 also includes a vacuum bag 24 surrounding the repair patch 12 and the acoustic facilitation layer 22 and configured to apply pressure thereto. The vacuum bag 24 may be formed of various materials, but is formed of nylon in an example embodiment.

The acoustic facilitation layer 22 of an example embodiment has an acoustic impedance that is between the acoustic impedance of air and the acoustic impedance of the repair patch 12. By way of example, air has an acoustic impedance of 0.00043 MegaRayleighs (MRayls), while a repair patch 12 formed of carbon fibers has an acoustic impedance of about 6.0 MRayls. As such, the acoustic facilitation layer 22 of this example embodiment has an acoustic impedance greater than 0.1 MRayls and less than 6.0 MRayls. In another embodiment, the acoustic facilitation layer 22 has an acoustic impedance that is between the acoustic impedance of air and the smaller of the acoustic impedances of the repair patch 12 and the vacuum bag 24. In the foregoing example involving a carbon fiber patch, the vacuum bag may be formed of nylon having an acoustic impedance of 2.90 MRayls. Thus, the acoustic facilitation layer 22 of this example embodiment has an acoustic impedance greater than 0.1 MRayls and less than 2.9 MRayls. Thus, the acoustic facilitation layer 22 has an acoustic impedance that is closer to respective acoustic impedances of the repair patch 12 and the vacuum bag 24 than the acoustic impedance of air is to the respective acoustic impedances of the repair patch and the vacuum bag so as to provide at least partial impedance matching. In an example embodiment, the acoustic facilitation layer 22 has an acoustic impedance of at least 1.0 MRayls and, more particularly, at least 1.43 MRayls and, even more particularly, at least 2.0 MRayls. In this regard, the acoustic impedance of the acoustic facilitation layer 22 of an example embodiment is closer to the acoustic impedance of the vacuum bag 24 than to the acoustic impedance of air.

Although the acoustic facilitation layer 22 may be formed of various materials, the acoustic facilitation layer of an example embodiment is formed of a rubber-like material in order to form intimate or direct contact with the first surface 12a of the repair patch 12, thereby advantageously eliminating an undesired layer of air. For example, the rubber-like material of the acoustic facilitation layer 22 may be formed of a rubber, such as a silicon-based synthetic rubber, a silicon rubber, a butyl rubber, neoprene, urethane rubber or a combination thereof. More particularly, the acoustic facilitation layer 22 of an example embodiment may be formed of Boeing Material Specification (BMS) 1-74 silicon-based synthetic rubber, Sylgard® 170 silicon rubber, PR-1201-Q sealant, Pellethane® urethane rubber or a room temperature vulcanizing (RTV)-60 rubber having 117.4 parts per hundred rubber (PHR).

As shown in FIG. 2, the assembly 20 of an example embodiment also includes an ultrasonic transducer 26 configured to introduce ultrasonic signals that propagate through the vacuum bag 24 and the acoustic facilitation layer 22 and then into the repair patch 12. Although an embodiment that employs through transmission inspection of a repair patch 12 is contemplated as described below, the assembly 20 of FIG. 2 is configured to inspect the repair patch 12 via a single-sided inspection. As such, the ultrasonic transducer 26 is also configured to receive echo signals returning from the repair patch 12.

The transmission equation for ultrasonic signals is based upon the impedance of the material through which the ultrasonic signals propagate. In an instance in which $Z_0$ and $Z_1$ define an interface therebetween, the transmission equation defining the percentage of ultrasonic signals that cross the interface is defined as $T=2Z_0/(Z_1+Z_0)$. In regards to the assembly 20 of FIG. 2, the total percentage transmission $T_{Total}$ of the ultrasonic signals is the product of the transmission across two interfaces, that is, the interface between the vacuum bag 24 having an acoustic impedance designated $Z_B$ and the acoustic facilitation layer 22 having an acoustic impedance designated $Z_F$ and the interface between the acoustic facilitation layer 22 and the repair patch 12 having an acoustic impedance designated $Z_C$ such that the total percentage transmission $T_{Total}$ is expressed as follows:

$$T_{Total} = \frac{2[Z_B]}{[Z_F + Z_B]} \frac{2[Z_F]}{[Z_C + Z_F]}$$

In an embodiment in which the vacuum bag 24 (designated "Bag") is formed of nylon 6-6 having an acoustic impedance $Z_B$ of 2.90 MRayls and the repair patch 12 (designated "Carbon") is comprised of carbon fibers embedded in an epoxy matrix having an acoustic impedance $Z_C$ of about 6 MRayls, the percentage transmission $T_{Total}$ of ultrasonic signals into the repair patch as a percentage of the total ultrasonic signals impinging upon the assembly 20 is illustrated below for assemblies having acoustic facilitation layers 22 formed with six different materials, namely, Sylgard® 170 silicon rubber, butyl rubber, neoprene, PR-1201-Q sealant, Pellethane® urethane rubber, and RTV-60 rubber having 117.4 PHR.

| | Vacuum Bag Nylon 6-6 $Z_B$ | Facilitator Layer $Z_F$ | Patch (Carbon) $Z_C$ | Transmission into Patch $T_{Total}$ |
|---|---|---|---|---|
| Bag/Air/Carbon (Scenario 1) | 2.90 | 0.00043 | 6.00 | 0.0% |
| Bag/Sylgard 170 Silicon rubber/Carbon | 2.90 | 1.34 | 6.00 | 49.9% |
| Bag/Butyl Rubber/Carbon | 2.90 | 2.00 | 6.00 | 59.2% |
| Bag/Neoprene/Carbon | 2.90 | 2.10 | 6.00 | 60.1% |
| Bag/[PR-1201-Q]/Carbon | 2.90 | 2.59 | 6.00 | 63.7% |
| Bag/Pellathane, Urethane rubber/Carbon | 2.90 | 2.62 | 6.00 | 63.9% |
| Bag/[RTV-60 117.4 PHR]/Carbon | 2.90 | 2.83 | 6.00 | 64.9% |

As shown, the acoustic impedance $Z_F$ of the different acoustic facilitation layers 22 varies from 1.34 MRayls to 2.83 MRayls with the percent transmission $T_{Total}$ of ultrasonic signals into the repair patch 12 correspondingly varying from 49.9% to 64.9%. As a point of comparison provided by the above table, for an assembly 20 including a vacuum bag 24 formed of nylon 6-6 and a repair patch 12 formed of carbon fibers embedded in an epoxy matrix without any acoustic facilitation layer and, instead, with an intervening layer of air having an acoustic impedance of 0.00043 MRayls surrounding the repair patch within the vacuum bag, the percent transmission $T_{Total}$ of the ultrasonic signals into the repair patch is approximately 0% due to the multiple interfaces between materials (vacuum bag/air and air/repair patch) having more greatly mismatched acoustic impedances.

In order to further facilitate the transmission of ultrasonic signals into the repair patch 12 during inspection of the repair patch, the vacuum bag 24 may be pressurized so as to apply pressure to the acoustic facilitation layer 22 and the repair patch. In this regard, the addition of pressure, such as approximately 10 to 11 psi increases the intimacy of the direct contact between the vacuum bag 24, the acoustic facilitation layer 22 and the repair patch 12. Further, the acoustic facilitation layer 22 compresses, thereby increasing its density and correspondingly increases its acoustic impedance $Z_F$. In this regard, acoustic impedance is a function of density and velocity as shown below:

$Z=\rho V$ wherein Z is the acoustic impedance in kilograms per seconds times meters squared, $\rho$ is the density in kilogram per cubic meter and V is the velocity of the ultrasonic signals in meters per second. Both the increased intimacy of the contact and the increased density of the acoustic facilitation layer 22 further improve the transmission of ultrasonic signals into the repair patch 12 during the inspection.

In an instance in which the compression of the acoustic facilitation layer 22 provided by pressurization of the vacuum bag 24 doubles the density $Z_F$ of the acoustic facilitation layer, the acoustic impedance of the acoustic facilitation layer would correspondingly double as shown below with the percentage $T_{TOTAL}$ of the ultrasonic signals transmitted into the repair patch during an inspection process correspondingly increasing such as to between 64.2% and 67.3% as shown below.

| | Vacuum Bag Nylon 6-6 $Z_B$ | Facilitator Layer $Z_F$ | Patch (Carbon) $Z_C$ | Transmission into Patch T |
|---|---|---|---|---|
| Bag/Sylgard 170 Silicon rubber/Carbon | 2.90 | 2.68 | 6.00 | 64.2% |
| Bag/Butyl Rubber/Carbon | 2.90 | 4.00 | 6.00 | 67.2% |
| Bag/Neoprene/Carbon | 2.90 | 4.20 | 6.00 | 67.3% |
| Bag/[PR-1201-Q]/Carbon | 2.90 | 5.18 | 6.00 | 66.5% |
| Bag/Pellathane, Urethane rubber/Carbon | 2.90 | 5.24 | 6.00 | 66.4% |
| Bag/[RTV-60 117.4 PHR]/Carbon | 2.90 | 5.66 | 6.00 | 65.8% |

By increasing the percentage of the ultrasonic signals that are transmitted into the repair patch 12, the echo signals returning from the repair patch are of a greater magnitude and allow improved signal-to-noise ratio and discrimination of features such as porosity, delamination and foreign object inclusion. Specifically, increasing the percentage of the ultrasonic signals allows better resolution of the back surface echo from the de-bulked patch 12, which is used to infer the presence of porosity, delaminations and foreign object inclusion.

As noted above, and shown in FIG. 3, the assembly 20 of an example embodiment can alternatively provide for through transmission inspection of a repair patch 12 in which ultrasonic signals are introduced through the first side 12a of the repair patch and the signals that exit through the second side 12b of the repair patch are captured and analyzed. In this embodiment, the assembly 20 also includes a second acoustic facilitation layer 28 disposed proximate the second surface 12b of the repair patch 12, opposite the first surface 12a of the repair patch through which the ultrasonic signals will be introduced. The first and second acoustic facilitation layers 22, 28 may be comprised of the same material. Alternatively, the first and second acoustic facilitation layers 22, 28 may be formed of different materials. In this example embodiment, the assembly 20 also include an ultrasonic receiver 30 configured to receive ultrasonic signals that exit the repair path 12 from the second side of the assembly, opposite the first side via which the ultrasonic transducer 26 introduces the ultrasonic signals. In this regard, ultrasonic signals introduced via the first surface 12a of the repair patch 12 by the ultrasonic transducer 26 are received upon exit from the second surface 12b of the repair path with the ultrasonic receiver 30. As such, the repair patch 12 can be subjected to a through transmission inspection, such as while the assembly 20 is held in a rack or submerged in a tank.

In a further example embodiment, and as shown in FIG. 4, the assembly 20 need not include a discrete acoustic facilitation layer, but, instead, the vacuum bag 24 may be at least partially comprised of an acoustic facilitation material, such as the rubber-like material described above. In an example embodiment, such as in an instance in which the repair patch 12 is to be subjected to a single-sided inspection, only the portion of the vacuum bag 24 proximate the first surface 12a of the repair patch need be comprised of the acoustic facilitation material 32 with the remainder of the vacuum bag comprised of another material, such as nylon. Alternatively, in an instance depicted in FIG. 5 in which the repair patch 12 is to be subjected to through transmission inspection, the entire vacuum bag 24 or at least those portions of the vacuum bag proximate the first and second opposed surfaces 12a, 12b of the repair patch 12 may be comprised of the acoustic facilitation material 32, 34. In either embodiment, however, intimate and direct contact is advantageously established between the vacuum bag 24 and the repair patch 12.

By incorporating the acoustic facilitation material into the construction of the vacuum bag 24 itself, the number of material interfaces are reduced, thereby reducing opportunities for reflection and improving transmission of ultrasonic signals into the repair patch 12. By way of example in which only the portion of the vacuum bag 24 proximate the first surface 12a of the repair patch 12 is formed of an acoustic facilitation material 32 having an acoustic impedance of between 1.34 MRayls and 2.83 MRayls and the remainder of the vacuum bag is formed of nylon 6-6, a single-side inspection of the repair patch 12 can be conducted. As indicated in the table below, for a repair patch 12 comprised of carbon fibers embedded in an epoxy resin and has an acoustic impedance of about 6 MRayls, the percent transmission $T_{TOTAL}$ of the ultrasonic signals into the repair patch for the vacuum bag 24 including six different types of acoustic facilitation materials 32 is defined below with the percent transmission $T_{TOTAL}$ ranging from 36.5% in an embodiment in which the acoustic facilitation material has an acoustic impedance of 1.34 MRayls to a percent transmission $T_{TOTAL}$ of 64.1% in an embodiment in which the acoustic facilitation material has an acoustic transmittance of 2.83 MRayls.

| | Acoustic Vacuum Bag $Z_X$ | Facilitator Layer $Z_F$ | Patch (Carbon) $Z_C$ | Transmission into Patch T |
|---|---|---|---|---|
| Bag of Sylgard 170 Silicon rubber/Carbon | 1.34 | N/A | 6.00 | 36.5% |
| Bag of Butyl Rubber/Carbon | 2.00 | N/A | 6.00 | 50.0% |
| Bag of Neoprene/Carbon | 2.10 | N/A | 6.00 | 51.9% |
| Bag of [PR-1201-Q]/Carbon | 2.59 | N/A | 6.00 | 60.3% |
| Bag of Pellathane, Urethane rubber/Carbon | 2.62 | N/A | 6.00 | 60.8% |
| Bag of [RTV-60 117.4 PHR]/Carbon | 2.83 | N/A | 6.00 | 64.1% |

As described above, in an instance in which the vacuum bag 24 is pressurized to an extent that the density of the acoustic facilitation material 32 from which a portion of the vacuum bag is formed doubles, the corresponding percentage $T_{TOTAL}$ of ultrasonic signals transmitted into the repair patch 12 correspondingly increases as shown below.

| | Acoustic Vacuum Bag $Z_X$ | Facilitator Layer $Z_F$ | Patch (Carbon) $Z_C$ | Transmission into Patch T |
|---|---|---|---|---|
| Bag of Sylgard 170 Silicon rubber/Carbon | 2.68 | N/A | 6.00 | 61.8% |

-continued

| | Acoustic Vacuum Bag $Z_X$ | Facilitator Layer $Z_F$ | Patch (Carbon) $Z_C$ | Transmission into Patch T |
|---|---|---|---|---|
| Bag of Butyl Rubber/Carbon | 4.00 | N/A | 6.00 | 80.0% |
| Bag of Neoprene/Carbon | 4.20 | N/A | 6.00 | 82.4% |
| Bag of [PR-1201-Q]/Carbon | 5.18 | N/A | 6.00 | 92.7% |
| Bag of Pellathane, Urethane rubber/Carbon | 5.24 | N/A | 6.00 | 93.2% |
| Bag of [RTV-60 117.4 PHR]/Carbon | 5.66 | N/A | 6.00 | 97.1% |

As will be noted, for at least some acoustic facilitation materials, such as RTV-60 sealant having a 117.4 PHR, the percent transmission $T_{TOTAL}$ of ultrasonic signals into the repair patch 12 approaches 100%, at least in instances in which the vacuum bag 24 is pressurized to an extent that the density of the acoustic facilitation material 32 doubles.

FIG. 6 illustrates a method 38 of inspecting a partially cured repair patch 12. The method 38 includes placing 40 the repair patch 12 within a vacuum bag 24 with an acoustic facilitation material proximate the first surface 12a of the repair patch. In one example embodiment in which the repair patch 12 is to be subjected to a single-sided inspection, the acoustic facilitation material may be disposed proximate the first surface 12a of the repair patch through which the ultrasonic signals will be introduced, such as by placing an acoustic facilitation layer 22 in contact with the surface of the repair patch. Thereafter, the repair patch 12 of this example embodiment is placed along with the acoustic facilitation layer 22 within the vacuum bag 24. Alternatively, in another embodiment in which the repair patch 12 is to be subjected to a through transmission inspection, acoustic facilitation material may be disposed proximate both the first surface 12a of the repair patch through which the ultrasonic signals will be introduced and the second surface 12b of the repair patch, opposite the first surface of the repair patch through which the ultrasonic signals will be introduced. In this example embodiment, the acoustic facilitation layers 22, 28 may be placed in contact with the respective surfaces 12a, 12b of the repair patch 12. Thereafter, the repair patch 12 with the acoustic facilitation layers 22, 28 disposed proximate opposite surfaces 12a, 12b thereof is placed within the vacuum bag 24. As yet another alternative, the vacuum bag 24 may be comprised, either completely or partially, of the acoustic facilitation material 32, 34, such that the acoustic facilitation material is disposed proximate the first surface 12a of the repair patch 12 through which ultrasonic signals will be introduced or opposite surfaces 12a, 12b of the repair patch through which ultrasonic signals will be introduced and will exit, respectively.

A method 38 of this example embodiment then transmits ultrasonic signals such that the ultrasonic signals are introduced into the repair patch 12 after propagating through the acoustic facilitation material. See block 42 of FIG. 6. For example, an ultrasonic transducer 26 may emit ultrasonic signals that are introduced into the repair patch 12. As a result of the inclusion of the acoustic facilitation material having an acoustic impedance that more closes approximates the acoustic impedance of the repair patch 12 than does the acoustic impedance of air and by establishing an intimate and direct contact between the acoustic fabrication material and the first surface 12a of the repair patch, the reflection of the ultrasonic signals is reduced and the percentage of the ultrasonic signals that are transmitted into the repair patch are increased, thereby improving the resulting inspection of the repair patch.

Thereafter, the ultrasonic signals are received following interaction with the repair patch 12 and propagation through the acoustic facilitation material. See block 44 of FIG. 6. In one embodiment, the repair patch 12 is subjected to a single-sided inspection such that the transmission and reception of the ultrasonic signals are performed from the same side of the repair patch, such as by the same ultrasonic transducer 25 or by the same array of ultrasonic transducers. Alternatively, the repair patch 12 is subjected to through transmission inspection such that the ultrasonic signals that exit from the second surface 12b of the repair patch 12, opposite the first surface 12a through which the ultrasonic signals are introduced into the repair patch, are received, such as by an ultrasonic receiver 30 distinct from the ultrasonic transducer that initially emitted the ultrasonic signals.

Based upon the ultrasonic signals that are received, the integrity of the repair patch 12 may be determined, such as by a computing device, e.g., a personal computer, desktop computer, networked computer, server or the like, that is in communication with the ultrasonic detector 30 and/or ultrasonic transducer 26 that received the ultrasonic signals following interaction with the repair patch. See block 46 of FIG. 6. In an example embodiment, the method 38 may also include determining whether the integrity of the repair patch satisfies a predefined criteria, such as determining whether the porosity of the repair patch satisfies a predefined criteria, whether the delaminations exceed a predetermined limit or a number of foreign object inclusions exceed a predetermined value. See block 48. For example, the computing device may be configured to determine whether the porosity of the repair patch 12 is less than the predefined criteria. In an instance in which the integrity of the repair patch 12 satisfies the predefined criteria, the repair patch may be applied to the structure with the repair patch then being completely cured. See block 50. In this instance, the repair patch 12 may be applied to the structure, such as with an intervening layer of epoxy, and then further cured in order to complete the repair. As before, the repair patch 12 and the resulting bond line may be inspected following installation of the repair patch to ensure that the resulting installation is satisfactory, although a greater percentage of the installed repair patches should be found to be satisfactory since only those repair patches that satisfy the predefined criteria following their partial curing in advance of the installation are actually installed. Further, the final inspection may, in some embodiments, concentrate solely on the bond line and near-proximity plies of the repair patch 12 to the bondline, simplifying the inspection method used for final inspection.

However, as shown in block 52, in an instance in which the integrity of the repair patch 12 fails to satisfy the predefined criteria, the repair patch may be discarded or reworked without installation of the repair patch to the structure. As such, in instances in which the repair patch 12 has a porosity that exceeds the predefined criteria and/or an excessive number of delaminations or foreign object inclusions, installation of the repair patch can be aborted, thereby avoiding an installation that would only be determined to be unsatisfactory, such as by having insufficient integrity, following the completion of the installation. Thus, the removal and rework of the structure followed by the reinstallation of another repair patch can be avoided in instances in which the repair patch 12 is determined to be unsatisfactory, such as by having excessive porosity, prior to the installation of the repair patch, thereby avoiding the undesired expenditure of resources and time to apply and then remove an unsatisfactory repair patch.

Many modifications and other aspects of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific aspects disclosed and that modifications and other aspects are intended to be included within the scope of the appended claims. Although specific teams are employed herein, they are used in a generic and descriptive sense only and not for purposes of limitation.

That which is claimed:

1. An assembly for inspecting a repair patch, the assembly comprising:
    a partially cured repair patch comprised of a composite material;
    an acoustic facilitation layer formed of a rubber and disposed in direct contact with a surface of the repair patch through which ultrasonic signals will be introduced; and
    a vacuum bag surrounding the repair patch and the acoustic facilitation layer such that the acoustic facilitation layer is within the vacuum bag, wherein the repair patch has been debulked and consolidated prior to being placed within the vacuum bag,
    wherein the acoustic facilitation layer has an acoustic impedance that is closer to respective acoustic impedances of the repair patch and the vacuum bag than the acoustic impedance of air is to the respective acoustic impedances of the repair patch and the vacuum bag.

2. An assembly according to claim 1 further comprising an ultrasonic transducer configured to introduce ultrasonic signals through the vacuum bag and the acoustic facilitation layer and then into the repair patch and to receive echo signals returning from the repair patch to facilitate single-sided inspection of the repair patch.

3. An assembly according to claim 2 wherein the vacuum bag is configured to apply pressure to the acoustic facilitation layer and the repair patch during the single-sided inspection of the repair patch.

4. An assembly according to claim 1 further comprising a second acoustic facilitation layer disposed proximate a second surface of the repair patch, opposite the surface of the repair patch through which ultrasonic signals will be introduced.

5. An assembly according to claim 4 further comprising:
    an ultrasonic transducer configured to introduce ultrasonic signals; and
    an ultrasonic receiver configured to receive ultrasonic signals following propagation through the vacuum bag, both acoustic facilitation layers and the repair patch so as to facilitate through transmission inspection of the repair patch.

6. As assembly according to claim 1 wherein the acoustic facilitation layer is comprised of a silicon-based synthetic rubber, a silicon rubber, a butyl rubber, neoprene, urethane rubber or a combination thereof.

7. An assembly for inspecting a repair patch, the assembly comprising:
    a partially cured repair patch comprised of a composite material; and
    a vacuum bag surrounding the repair patch and making direct contact with the repair patch so as to define an interface directly between the vacuum bag and the repair patch, wherein the repair patch has been debulked and consolidated prior to being placed within the vacuum bag, and wherein the vacuum bag is comprised of an acoustic facilitation material formed of a rubber that is in direct contact with the repair patch, and wherein the acoustic facilitation material has an acoustic impedance that is closer to the acoustic impedance of the repair patch than the acoustic impedance of air is to the acoustic impedance of the repair patch.

8. An assembly according to claim 7 further comprising an ultrasonic transducer configured to introduce ultrasonic signals through the vacuum bag and then into the repair patch and to receive echo signals returning from the repair patch to facilitate single-sided inspection of the repair patch.

9. An assembly according to claim 8 wherein the vacuum bag is configured to apply pressure to the repair patch during the single-sided inspection of the repair patch.

10. An assembly according to claim 7 further comprising an ultrasonic transducer configured to introduce ultrasonic signals that propagate through the vacuum bag and the repair patch so as to facilitate through transmission inspection of the repair patch.

11. As assembly according to claim 7 wherein the vacuum bag is comprised of a silicon-based synthetic rubber, a silicon rubber, a butyl rubber, neoprene, urethane rubber or a combination thereof.

12. A method of inspecting a partially cured repair patch comprising:
    placing the repair patch within a vacuum bag such that an acoustic facilitation material formed of a rubber makes direct contact with the repair patch so as to define an interface directly between the acoustic facilitation material and the repair patch, wherein the repair patch has been debulked and consolidated prior to being placed within the vacuum bag, and wherein the acoustic facilitation material has an acoustic impedance that is closer to the acoustic impedance of the partially cured repair patch than the acoustic impedance of air;
    transmitting ultrasonic signals from outside the vacuum bag such that the ultrasonic signals are introduced into the repair patch after propagating through the acoustic facilitation material;
    receiving the ultrasonic signals following interaction with the repair patch and propagation through the acoustic facilitation material; and
    determining integrity of the repair patch based upon the ultrasonic signals that are received.

13. A method according to claim 12 further comprising disposing an acoustic facilitation layer comprised of the acoustic facilitation material in direct contact with the surface of the repair patch through which the ultrasonic signals will be introduced, and wherein placing the repair patch within the vacuum bag comprises placing the repair patch and the acoustic facilitation layer within the vacuum bag.

14. A method according to claim 13 wherein transmitting and receiving the ultrasonic signals are performed from a single side of the repair patch.

15. A method according to claim 12 further comprising:
    disposing an acoustic facilitation layer comprised of the acoustic facilitation material in direct contact with the surface of the repair patch through which the ultrasonic signals will be introduced; and disposing a second acoustic facilitation layer proximate a second surface of the repair patch, opposite the surface of the repair patch through which ultrasonic signals will be introduced, wherein placing the repair patch within the vacuum bag comprises placing the repair patch with the acoustic facilitation layers disposed proximate opposite surfaces thereof within the vacuum bag.

16. A method according to claim 15 wherein receiving the ultrasonic signals comprises receiving the ultrasonic signals that exit from a surface of the repair patch, opposite the surface through which the ultrasonic signals are introduced into the repair patch.

17. A method according to claim 12 wherein the vacuum bag is comprised of the acoustic facilitation material.

18. A method according to claim 12 wherein the acoustic facilitation material is comprised of a silicon-based synthetic rubber, a silicon rubber, a butyl rubber, neoprene, urethane rubber or a combination thereof.

19. A method of inspecting a partially cured repair patch comprising:

determining whether integrity of the repair patch satisfies a predefined criteria;

in an instance in which the integrity of the repair patch satisfies the predefined criteria, applying the repair patch to a structure and further curing the repair patch by:

placing the repair patch within a vacuum bag such that an acoustic facilitation material formed of a rubber makes direct contact with the repair patch so as to define an interface directly between the acoustic facilitation material and the repair patch, wherein the acoustic facilitation material has an acoustic impedance that is closer to the acoustic impedance of the partially cured repair patch than the acoustic impedance of air;

transmitting ultrasonic signals from outside the vacuum bag such that the ultrasonic signals are introduced into the repair patch after propagating through the acoustic facilitation material;

receiving the ultrasonic signals following interaction with the repair patch and propagation through the acoustic facilitation material; and determining the integrity of the repair patch based upon the ultrasonic signals that are received; and in an instance in which the integrity of the repair patch fails to satisfy the predefined criteria, discarding or reworking the repair patch.

20. A method according to claim 19 wherein the repair patch has been debulked and consolidated prior to being placed within the vacuum bag.

* * * * *